United States Patent
Bachinski

[11] Patent Number: 6,001,124
[45] Date of Patent: Dec. 14, 1999

[54] OBLIQUE-ANGLE GRAFT CONNECTORS

[75] Inventor: Thomas J. Bachinski, Lakeville, Minn.

[73] Assignee: Vascular Science, Inc., Minneapolis, Minn.

[21] Appl. No.: 08/948,162

[22] Filed: Oct. 9, 1997

[51] Int. Cl.$^6$ ..................................................... A61F 2/06
[52] U.S. Cl. .................... 623/1; 623/12; 606/194
[58] Field of Search .................... 623/1, 12; 606/194, 606/192, 108, 195

[56] References Cited

U.S. PATENT DOCUMENTS

| | | | |
|---|---|---|---|
| 3,155,095 | 11/1964 | Brown | 623/1 |
| 4,214,587 | 7/1980 | Sakura, Jr. | 128/334 R |
| 4,503,569 | 3/1985 | Dotter | 3/1.4 |
| 4,592,754 | 6/1986 | Gupte et al. | 623/1 |
| 4,617,932 | 10/1986 | Kornberg | 128/334 R |
| 4,665,906 | 5/1987 | Jervis | 128/92 YN |
| 4,787,899 | 11/1988 | Lazarus | 623/1 |
| 5,102,417 | 4/1992 | Palmaz | 623/11 |
| 5,104,399 | 4/1992 | Lazarus | 623/1 |
| 5,135,467 | 8/1992 | Citron | 600/16 |
| 5,211,658 | 5/1993 | Clouse | 623/1 |
| 5,211,683 | 5/1993 | Maginot | 128/898 |
| 5,275,622 | 1/1994 | Lazarus et al. | 623/1 |
| 5,304,220 | 4/1994 | Maginot | 623/1 |
| 5,316,023 | 5/1994 | Palmaz et al. | 128/898 |
| 5,354,336 | 10/1994 | Kelman et al. | 623/6 |
| 5,387,235 | 2/1995 | Chuter | 623/1 |
| 5,397,345 | 3/1995 | Lazarus | 623/1 |
| 5,443,497 | 8/1995 | Venbrux | 623/1 |
| 5,456,712 | 10/1995 | Maginot | 623/1 |
| 5,489,295 | 2/1996 | Piplani et al. | 623/1 |
| 5,496,365 | 3/1996 | Sgro | 606/194 |
| 5,507,769 | 4/1996 | Marin et al. | 606/198 |
| 5,522,880 | 6/1996 | Barone et al. | 623/1 |
| 5,545,214 | 8/1996 | Stevens | 623/2 |
| 5,667,486 | 9/1997 | Mikulich et al. | 623/12 |
| 5,695,504 | 12/1997 | Gifford, III et al. | 606/153 |
| 5,707,387 | 1/1998 | Wijay | 623/1 |
| 5,735,871 | 4/1998 | Srgo | 606/194 |
| 5,741,293 | 4/1998 | Wijay | 623/12 |
| 5,800,520 | 9/1998 | Fogarty et al. | 623/1 |

FOREIGN PATENT DOCUMENTS

| | | | |
|---|---|---|---|
| 670 239 | 1/1994 | Australia | A61F 2/06 |
| 0 539 237 A1 | 4/1993 | European Pat. Off. | A61F 2/06 |
| 0 680 734 A2 | 1/1995 | European Pat. Off. | A61F 2/06 |
| 0 637 454 A1 | 2/1995 | European Pat. Off. | A61M 25/10 |
| 0 684 022 A2 | 11/1995 | European Pat. Off. | A61F 2/06 |
| WO 96/18361 | 6/1996 | WIPO | A61F 2/06 |
| WO 97/13463 | 4/1997 | WIPO | A61B 17/00 |
| WO 97/13471 | 4/1997 | WIPO | A61B 19/00 |

Primary Examiner—Bruce E. Snow
Attorney, Agent, or Firm—Fish & Neave; Robert R. Jackson; G. Victor Treyz

[57] ABSTRACT

Connectors are provided for attaching flexible tubular grafts to the body organ tubing of a patient at oblique angles. The connector structures may be formed from two elongated members connected by a series of struts. Wire hooks welded to the connector may be used to engage the graft and the body organ tubing when the connector is used to attach the graft to the body organ tubing. The struts are bendable so that the elongated members can be compressed toward each other when it is desired to install a graft by placing the graft and the connector in a delivery tube. When the connector and graft are released from the delivery tube at the installation site, at least the open end of the connector adjacent to the body organ tubing has an oval shape for insertion into and attachment to an oval aperture in the body organ tubing. The elongated members are longitudinally shifted relative to each other so that the connector is angled obliquely to support attachment of the graft to the body organ tubing at an oblique angle.

18 Claims, 6 Drawing Sheets

OBLIQUE-ANGLE GRAFT CONNECTORS

BACKGROUND OF THE INVENTION

This invention relates to replacing or supplementing a patient's natural body organ tubing by installing tubular graft structures. More particularly, the invention relates to connector structures for making oblique-angle connections between such tubular graft structures and body organ tubing.

A patient's weakened or diseased body organ tubing can often be repaired by replacing or supplementing the patient's existing natural body organ tubing with an artificial graft structure. One suitable type of artificial graft structure uses a tubular nitinol mesh frame covered with a silicone coating, as described in Goldsteen et al. U.S. Pat. application Ser. No. 08/745,618, filed Nov. 7, 1996. Such grafts are highly flexible, so they recover their shape after being stretched. Accordingly, a graft of this type may be stretched axially to reduce its radial dimension and then installed in a patient intraluminally (e.g., through an existing vein or artery). Once delivered to the proper location within the patient, the axially stretched graft may be released, whereupon it expands to regain its original shape.

In addition, flexible artificial grafts may be made distensible like natural body organ tubing to help reduce clot formation when used in vascular applications. Flexible artificial grafts may also be made biocompatible by adjusting their porosity and the composition of their coatings.

Various connector structures may be used to attach flexible artificial grafts to a patient's body organ tubing. For example, a graft may be surgically attached to body organ tubing with sutures. To install a graft intraluminally, a pronged ring may be expanded from within the end of the graft, thereby piercing the graft and attaching it to surrounding body organ tubing. Barbed flaps and wire hooks may also be used to attach grafts to body organ tubing. Connector structures of these types and other suitable connector structures are described in the above-mentioned Goldsteen et al. U.S. Pat. application Ser. No. 08/745,618, filed Nov. 7, 1996 and in Bachinski et al. U.S. Pat. application Ser. No. 08/839,199, filed Apr. 23, 1997. Wire-based connector structures suitable for attaching grafts to body organ tubing at oblique angles are described in Berg et al. U.S. Pat. application Ser. No. 08/946,742, filed Oct. 9, 1997.

Although connector structures of these types have various useful features, it would be desirable if other connector structures were available, particularly connectors for making oblique-angle connections between tubular grafts and body organ tubing.

It is therefore an object of the present invention to provide improved connector structures for attaching grafts to a patient's body organ tubing at oblique angles.

SUMMARY OF THE INVENTION

This and other objects of the invention are accomplished in accordance with the principles of the present invention by providing connectors for attaching flexible tubular grafts to the body organ tubing of a patient. The connectors allow grafts to be attached to body organ tubing at oblique angles (i.e., angles other than right angles).

The connector structures may be formed from two elongated members connected by a series of struts. The struts are bendable so that the elongated members can be compressed toward each other during intraluminal installation of a graft and connector (e.g., through the vascular system of a patient). During such an installation, the compressed connector and graft are placed in a delivery tube. The connector has attachment members such as heat-set nitinol wire hooks that are welded or otherwise connected to the elongated tubular members. When the graft and connector are released from the delivery tube, the hooks engage the graft and the body organ tubing of the patient, thereby attaching the graft to the body organ tubing.

At least the open end of the released connector that is adjacent to the body organ tubing has an oval shape that matches the oval shape of the body organ tubing aperture into which the connector and graft are inserted during graft installation. The elongated members of the connector are longitudinally shifted with respect to one another, so that when the oval open end of the connector is installed in the oval aperture in the body organ tubing an oblique angle is formed between the shared longitudinal axis of the graft and the connector and the longitudinal axis or surface of the body organ tubing.

Slots may be formed in the connector to make the connector distensible. The slots may be formed using laser cutting, water jet cutting, electrode discharge machining, or chemical etching. The connector may be fabricated by cutting the connector from a tube of nitinol as a single piece, shaping the connector into a desired final shape, and heat treating the connector to set the connector in the desired final shape.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
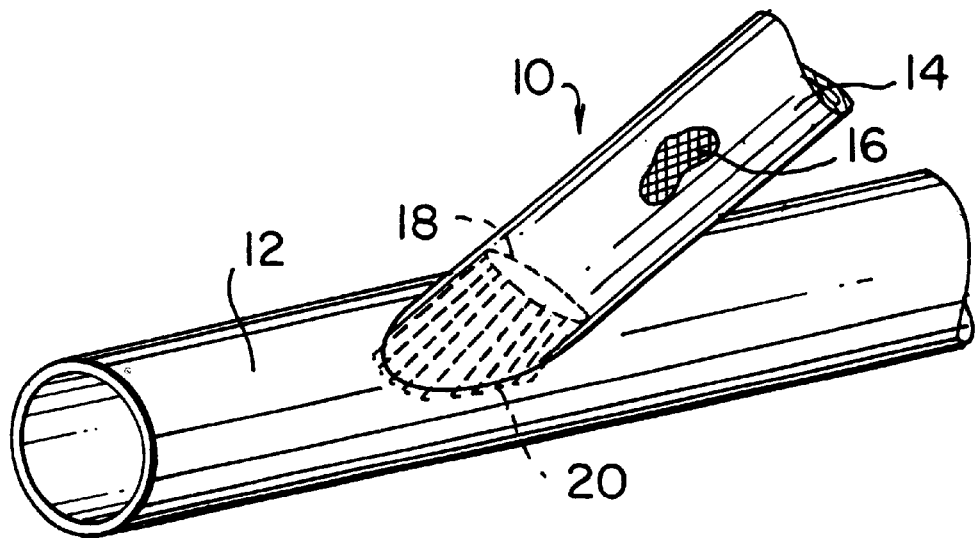
FIG. 1 is a perspective view of a graft attached to a length of body organ tubing at an oblique angle with a connector in accordance with the present invention.

A graft 10 connected to body organ tubing 12 in accordance with the present invention is shown in FIG. 1. Graft 10 is preferably an artificial flexible tubular structure, although the connector arrangements of the present invention may be used with natural grafts if desired. Artificial flexible tubular graft 10 may be formed from a flexible coating 14 covering a flexible frame 16. The preferred materials for forming frame 16 are metals, although polymeric materials may also be used. The presently most preferred material is a braid of nitinol wire.

Graft 10 is connected to body organ tubing 12 using connector 18. Connectors such as connector 18 are preferably formed from the same type of flexible material as frame 16 (e.g., nitinol). Nitinol is heat sensitive, so connectors 18 of various shapes may be formed by cutting, bending, and otherwise forming the nitinol material that makes up the connector into a desired shape and applying a heat treatment to set the nitinol in that shape.

Coating 14 is preferably an elastic biocompatible material such as silicone, which fills the apertures formed by the wires in frame 16. Other materials that may be used for coating 14 include polymeric materials such as stretchable urethane, stretchable polytetrafluoroethylene (PTFE), natural rubber, and the like.

If desired, coating 14 can be formed with microscopic pores to help improve biocompatibility. A preferred method of providing a desired porosity is to make coating 14 from an elastic material that is mixed with particles of a material that can be removed (e.g., by vaporization) after coating 14 has been applied to frame 16. When the particles are removed, voids are left in coating 14 that give it porosity.

Graft 10 may be provided with additional coatings such as medicated coatings, hydrophilic coatings, smoothing coatings, collagen coatings, human cell seeding coatings, etc., as described in the above-mentioned Goldsteen et al. U.S. Pat. application Ser. No. 08/745,618, filed Nov. 7, 1996, which is hereby incorporated by reference herein in its entirety. The above-described preferred porosity of coating 12 may help graft 10 to retain these coatings.

In the illustrative example of FIG. 1, graft 10 has been used to form a connection to a tubular length of body organ tubing 12. Graft 10 may be used to connect portions of body organ tubing of any suitable shape. As defined herein, the term "body organ tubing" generally refers to elongated fluid-containing body organ tissues such as blood vessels and the like and to similar but less elongated body organ tissue structures such as portions of the heart wall. Body organ tubing 12 may be vascular tubing or any other type of body organ tubing.

Connector 18 is used to attach graft 10 to body organ tubing 12 at an oblique angle (i.e., the angle between the longitudinal axis of graft 10 and the longitudinal axis or surface of the body organ tubing 12 is not a right angle). Because the angle of attachment between graft 10 and body organ tubing 12 is oblique, the periphery 20 of the connection between graft 10 and body organ tubing 12 is shaped like an oval.

Figure 2:
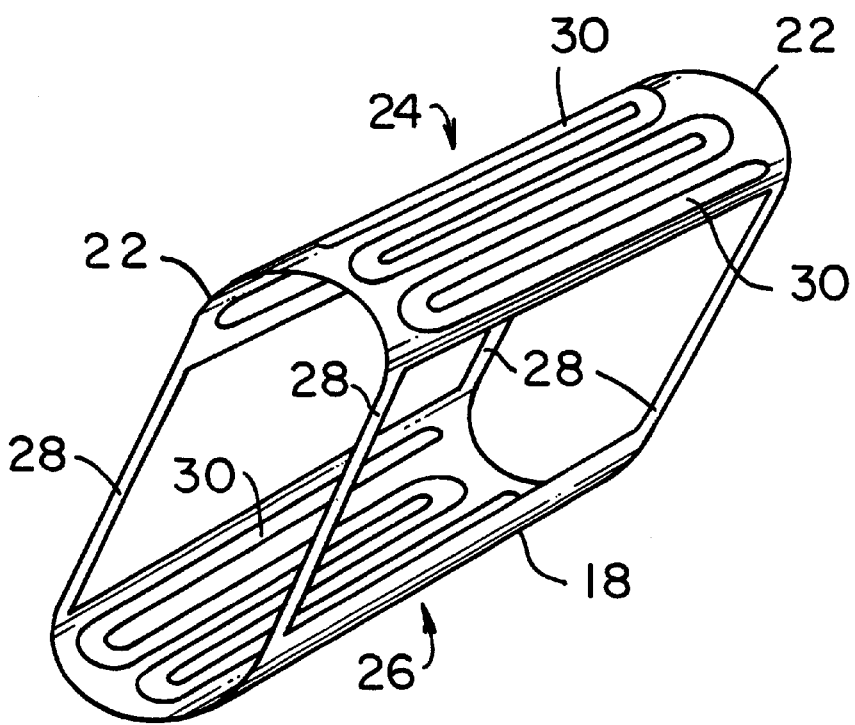
FIG. 2 is a perspective view of an illustrative connector in accordance with the present invention.

As shown in FIG. 2, the open ends 22 of connector 18 are also ovals, so that connector 18 accommodates the oval shape of periphery 20 when connector 18 is used to form an oblique-angle connection between graft 10 and body organ tubing 12. Connector 18 is formed from two elongated members 24 and 26 formed from portions of a tube. Elongated members 24 and 26 are joined by a connection structure formed from struts 28.

Members 24 and 26 have longitudinal slots 30 which may provide connector 18 with distensibility (i.e., the ability to expand and contract in response to variations in the pressure of the fluid contained within connector 18 during use). If desired, slots 30 may be continuous serpentine longitudinal slots provided in the form of continuous serpentine cut-away portions, as shown in FIG. 2.

Struts 28 are preferably integrally formed with members 24 and 26. If desired, however, struts 28 may be separate support members that are attached to members 24 and 26 (e.g., by welding).

Figure 3:
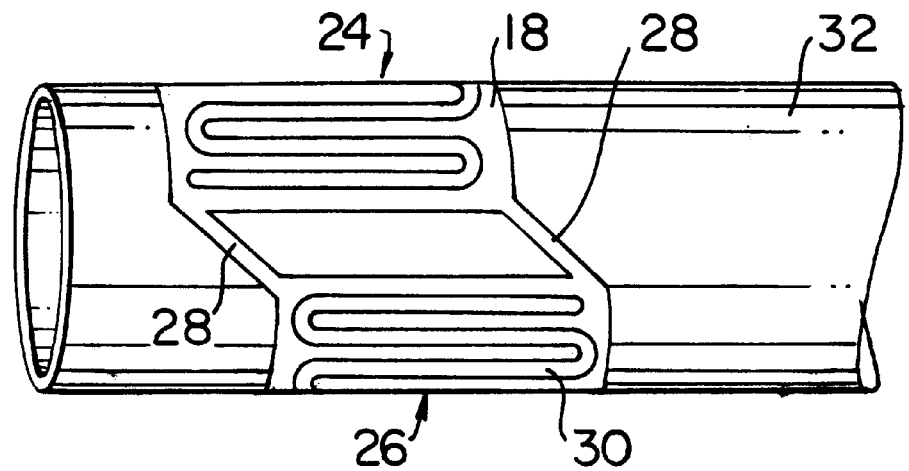
FIG. 3. is a side view showing how a connector in accordance with the present invention may be cut from a metal tube as a single piece.

One way in which to form members 24 and 26 and struts 28 as an integral structure is to cut connector 18 from a hollow tube of nitinol 32 in a single piece, as shown in FIG. 3. After connector 18 is cut from tube 32, it may be desirable to bend, stretch, and heat set connector 18 into the final shape shown in FIG. 2. Tube 32 does not need to be perfectly round in cross section nor do elongated members 24 and 26 need to be shaped like portions of perfectly round tubes, provided that connector 18 is deployed with one elongated member axially shifted relative to the other elongated member, so that at least one end of connector 18 is approximately oval in shape and connector 18 supports attachment of graft 10 to body organ tubing 12 at an oblique angle.

Figure 4:
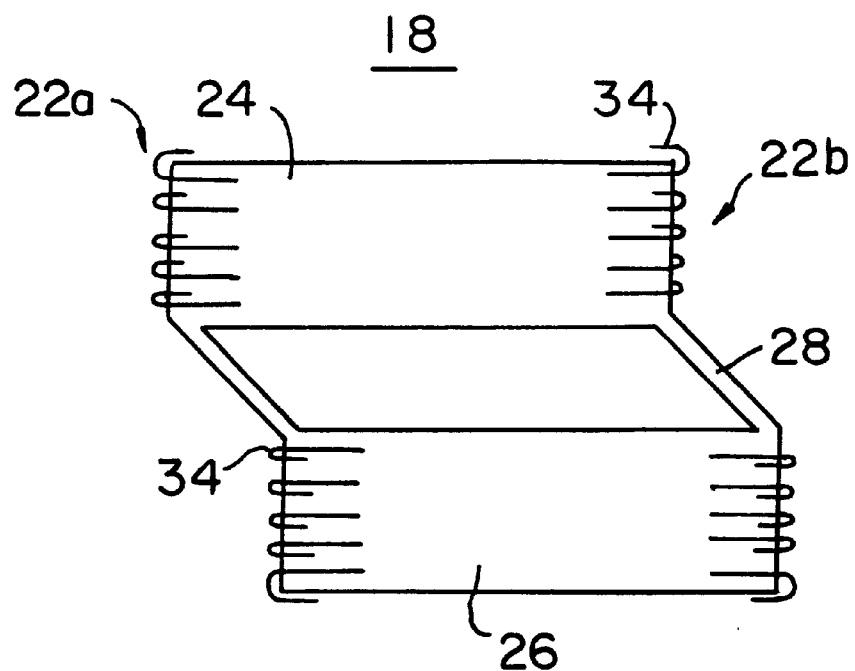
FIG. 4 is a side view of an illustrative connector showing how wire hooks may be provided to attach the connector to body organ tubing and a graft in accordance with the present invention.

In order to attach connector 18 to body organ tubing 12 and graft 10, connector 18 is preferably provided with attachment members such as hooks 34 of FIG. 4. Hooks 34 may be formed from bent and heat-set nitinol wire strands that are attached to connector 18 by welding or other suitable attachment scheme. Hooks 34 at open end 22a of connector 18 are used to attach connector 18 to body organ tubing 12 and may help to attach graft 10 to body organ tubing 12. Hooks 34 at open end 22b of connector 18 are used to attach connector 18 to graft 10.

Figure 5A:
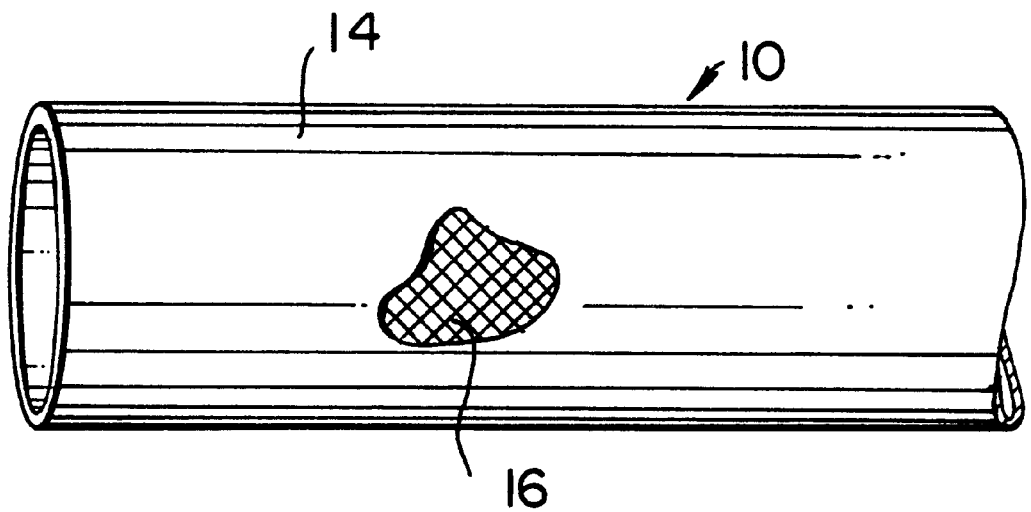
FIG. 5a is a side view of a graft with a right-angle end for attachment to a portion of body organ tubing.
Figure 5B:
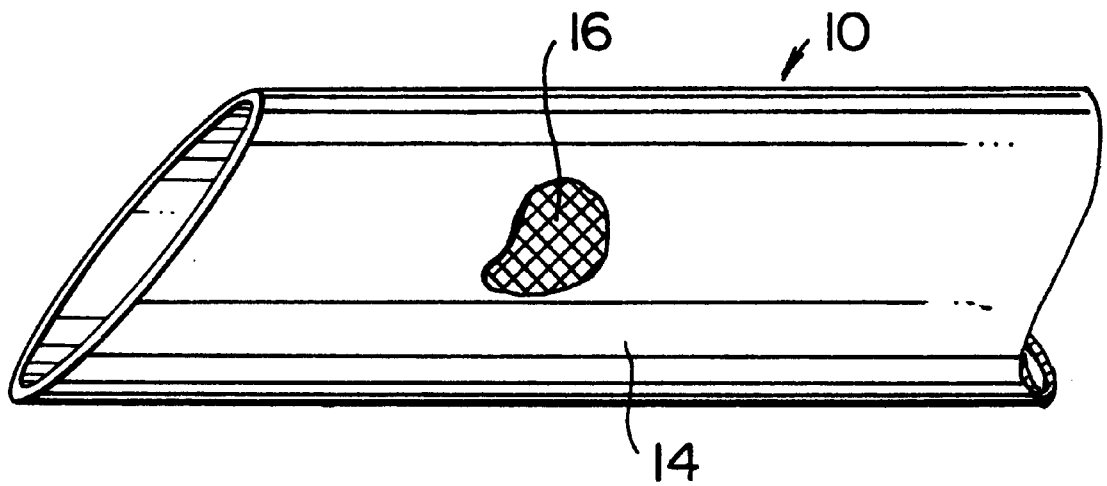
FIG. 5b is a side view of a graft with an oblique (non-right-angle) end for attachment to a portion of body organ tubing.

If desired, the end of graft 10 used in forming the connection between graft 10 and body organ tubing 12 may be formed at a right angle relative to the longitudinal axis of graft 10, as shown in FIG. 5a. Alternatively, the end of graft 10 used in forming the connection between graft 10 and body organ tubing 12 may be formed at an oblique angle relative to the longitudinal axis of graft 10, as shown in FIG. 5b. The right-angle arrangement of FIG. 5a is relatively easy to form and need not be rotationally aligned with respect to connector 18 prior to installation in a patient. With the arrangement of FIG. 5b, the longitudinally projecting tip of graft 10 must be aligned with the elongated member 24 or 26 of connector 18 that is longitudinally shifted toward the attachment site. However, the arrangement of FIG. 5b may alleviate some of the tension that might otherwise be created in graft 10 when the end of graft 10 in FIG. 5a is stretched into the shape used for an oblique-angle connection.

Figure 6:
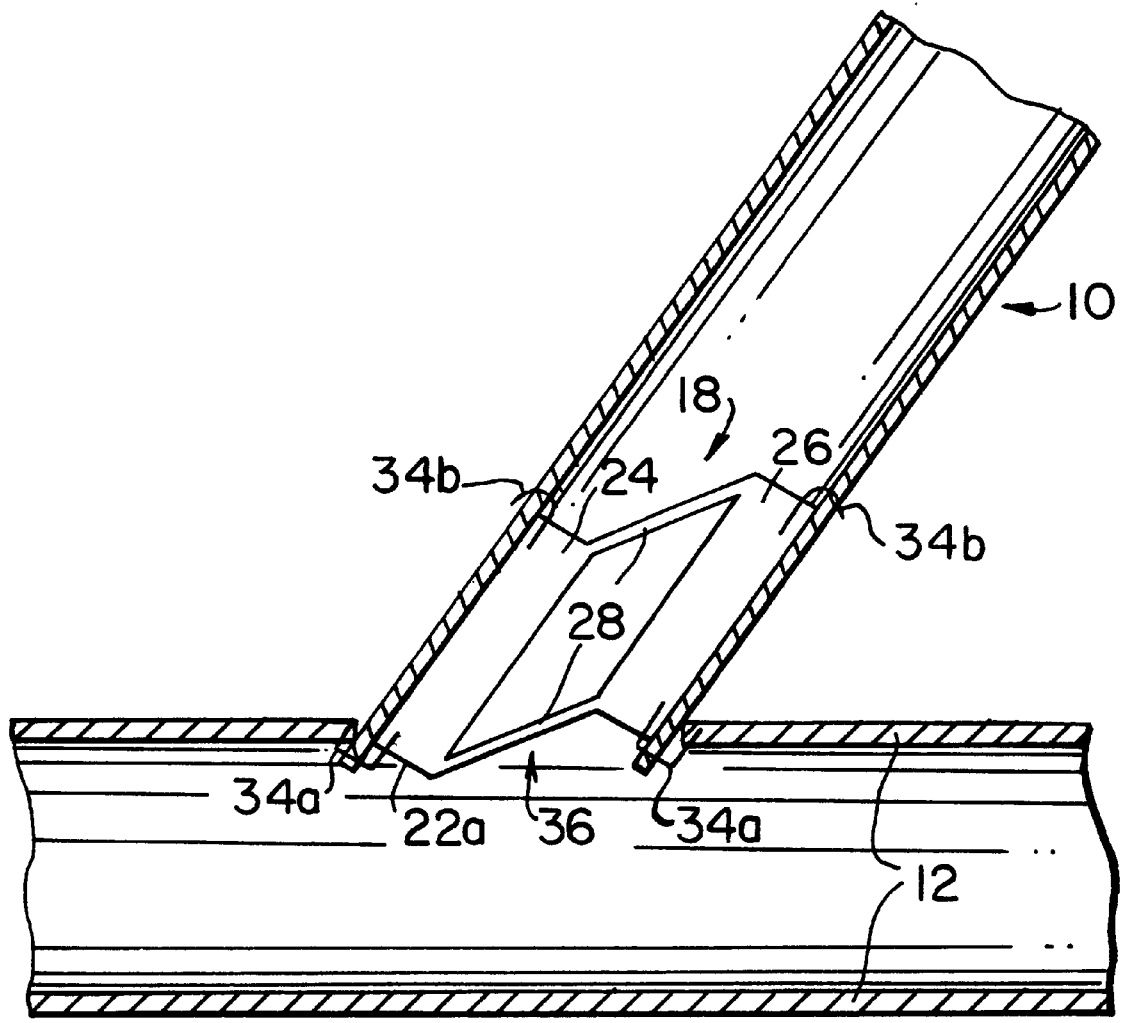
FIG. 6 is a sectional view of a graft attached to a portion of body organ tubing at an oblique angle using an illustrative connector in accordance with the present invention.

Regardless of the particular shape used for the end of graft 10, graft 10 is preferably attached to body organ tubing 12 as shown in FIG. 6. Prior to attachment, an aperture 36 having approximately the shape of an oval (in the dimension perpendicular to the page) is formed in the upper wall of body organ tubing 12 by any suitable technique. Graft 10 surrounds connector 18 and is attached to connector 18 by hooks 34a and 34b. If desired, hooks like hooks 34a and 34b may be provided at other axial locations on connector 18 to further secure graft 10 to connector 18. At open end 22a, hooks 34a penetrate the portion of body organ tubing 12 surrounding aperture 36, thereby attaching graft 10 and connector 18 to body organ tubing 12. Because elongated member 24 is shifted longitudinally with respect to elongated member 26, connector 18 supports attachment of graft 10 to body organ tubing 12 at an oblique angle.

If desired, graft 10 may be delivered to an attachment site in a patient intraluminally. An illustrative arrangement for attaching graft 10 to body organ tubing 14 is shown in FIGS.

Figure 7A:
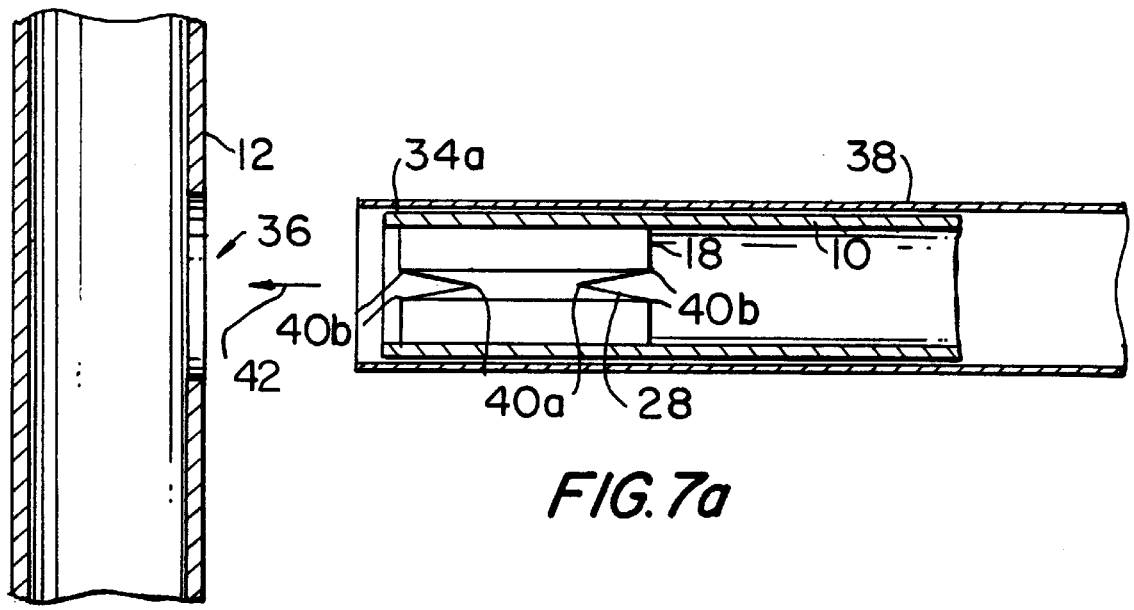
FIGS. 7a and 7b are sectional views of an illustrative arrangement for attaching a graft to body organ tubing using a connector in accordance with the present invention.

7a and 7b. Prior to attachment, graft 10 is loaded into delivery tube 38 (which can be inserted into a patient intraluminally) by compressing connector 18 to reduce the lateral spacing of elongated members 24 and 26. During compression of connector 18, struts 28 bend at hinge points 40a and 40b, as shown in FIG. 7a. This allows the relative longitudinal shift of elongated members 24 and 26 to be reduced or removed entirely during compression of connector 18, so that connector 18 fits inside a delivery tube with a right-angle end. Graft 10 may be radially compressed by axial stretching. Delivery tube 38 and the compressed graft 10 and connector 18 are advanced in direction 42 through aperture 36. During insertion of delivery tube 38 into aperture 36, delivery tube 38 holds hooks 34a radially inward and out of the way.

Figure 7B:
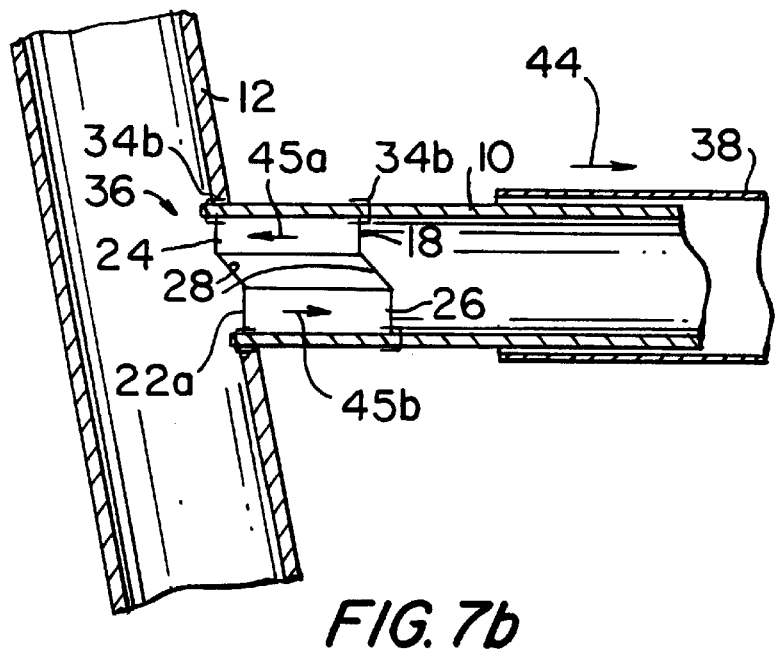

As shown in FIG. 7b, once open end 22a of connector 18 and the associated end of graft 10 are advanced through aperture 36 in body organ tubing 12, delivery tube 38 can be drawn backward in direction 44. Drawing delivery tube 38 backward releases connector 18, which expands as struts 28 straighten to assume their normal straight configuration. Wires 34a are also released and assume their normal configuration by expanding and piercing the portion of body organ tubing 12 surrounding aperture 36 to hold graft 10 in place.

Releasing connector 18 causes elongated members 24 and 26 to axially shift relative to one another as shown by arrows 45a and 45b. Accordingly, open end 22a of connector 18 forms an oval shape and connector 18 is angled properly to support an oblique-angle connection between graft 10 and body organ tubing 12, as shown in FIG. 7b.

If the other end of graft 10 has a connector 18, the same attachment process may be performed at that end of graft 10 by inserting the preloaded delivery tube 38 through another aperture in body organ tubing 12 and removing delivery tube 38 through that aperture (rather than moving delivery tube 38 away from that aperture 36 as shown in FIGS. 7a and 7b).

Figure 8:
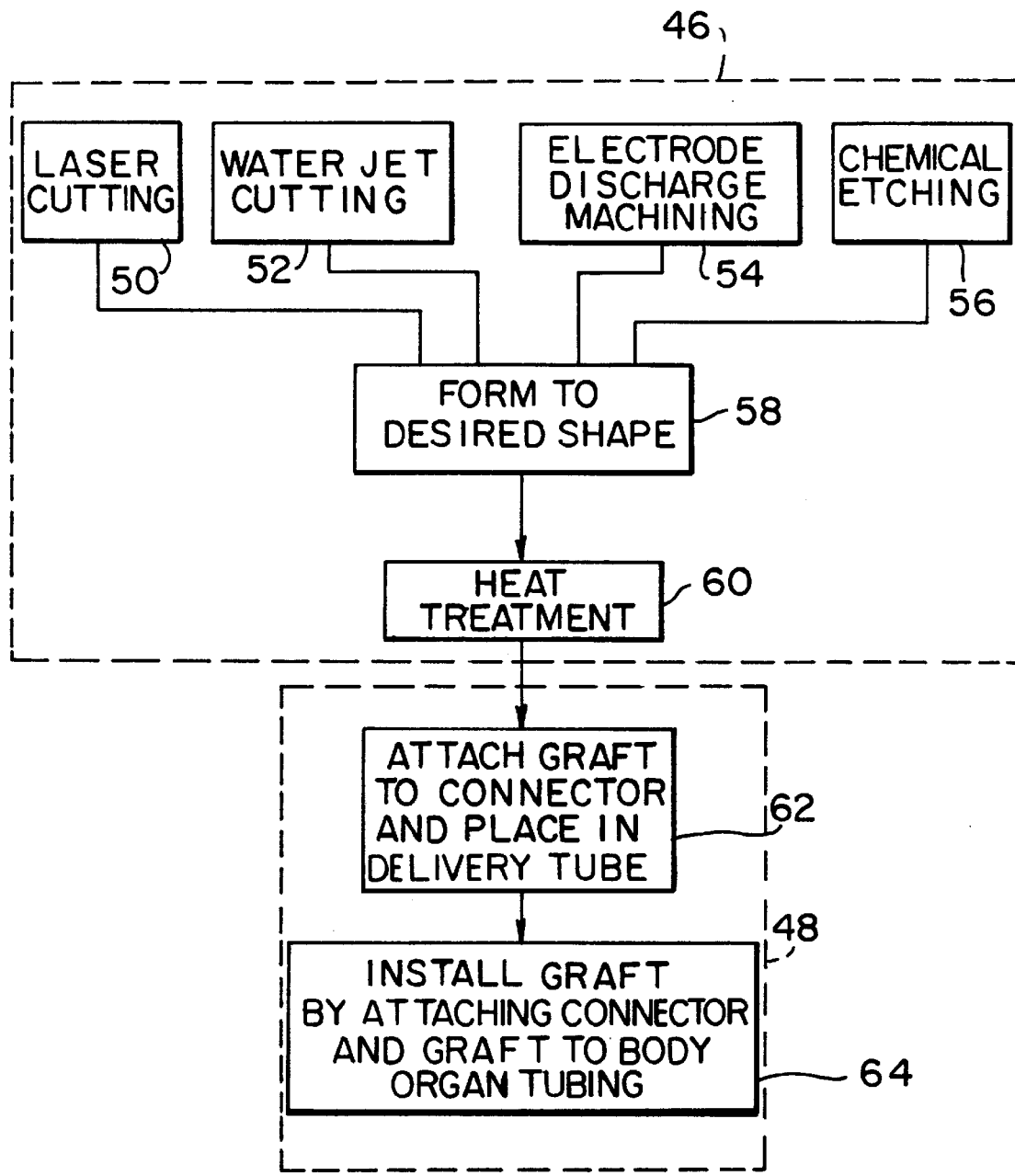
FIG. 8 is a flow chart of illustrative steps involved in fabricating and installing connectors in accordance with the present invention.

Illustrative steps involved in fabricating and installing grafts 10 using connectors 18 of the present invention are shown in FIG. 8. Steps 46 are connector fabrication steps. Steps 48 are graft and connector installation steps.

Connector 18 is preferably formed by cutting connector 18 from tubing of nitinol or other suitable material as a single piece, as shown in FIG. 3. As shown in FIG. 8, such cutting may involve laser cutting (step 50), water jet cutting (step 52), electrode discharge machining (step 54), or chemical etching (step 56). Connector 18 may then be formed to its desired final shape at step 58. At step 60, a heat treatment may be applied to connector 18 to heat set connector 18 into its final shape.

At step 62, graft 10 is attached to connector 18 (e.g., using hooks 34) and placed in delivery tube 38. At step 64, graft 10 and connector 18 are inserted into aperture 36 in body organ tubing 12 and delivery tube 38 is removed to attach graft 10 and connector 18 to body organ tubing 12. Removing delivery tube 38 releases connector 18 so that the open end 22a of connector 18 forms an oval shape (as shown in FIG. 2). In addition, elongated members 24 and 26 shift longitudinally with respect to each other so that connector 18 supports an oblique-angle connection between graft 10 and body organ tubing 12 (i.e., the shared longitudinal axis of connector 18 and graft 10 is obliquely-angled relative to the longitudinal axis of body organ tubing 12).

It will be understood that the foregoing is only illustrative of the principles of the invention, and that various modifications can be made by those skilled in the art without departing from the scope and spirit of the invention.

The invention claimed is:

1. A connector for forming an oblique-angle connection between a flexible tubular graft and an aperture in a portion of a patient's body organ tubing wherein the connector has a length, the connector comprising:

a first elongated member extending substantially the length of the connector and having first and second edges;

a second elongated member having first and second edges, wherein the first and second edges of the first elongated member are substantially not in contact with the first and second edges of the second elongated member; and a connection structure connecting the first and second elongated members parallel to each other, the first and second members being laterally spaced and longitudinally shifted with respect to each other so that the connector has at least one substantially oval open end for insertion in the aperture and supports connection of the flexible tubular graft to a portion of the body organ tubing of the patient at an oblique angle.

2. The connector defined in claim 1 wherein the first and second elongated members comprise portions of a tube.

3. The connector defined in claim 1 wherein the first and second elongated members comprise portions of a nitinol tube.

4. The connector defined in claim 1 wherein the connection structure comprises a plurality of struts connected between the first and second elongated members.

5. The connector defined in claim 1 further comprising attachment members connected to the first and second elongated members for engaging the flexible tubular graft.

6. The connector defined in claim 1 further comprising attachment members connected to the first and second elongated members for engaging the body organ tubing.

7. The connector defined in claim 1 wherein:

the first and second elongated members each have two ends; and the connector further comprises attachment members connected to the first and second elongated members at both of the two ends of the first and second elongated members for engaging the flexible tubular graft and the body organ tubing.

8. The connector defined in claim 1 wherein:

the first and second elongated members each have two ends; and the connector further comprises wire hooks connected to the first and second elongated members at both ends of the first and second elongated members for engaging the flexible tublar graft and the body organ tubing.

9. The connector defined in claim 1 wherein the first and second elongated members and the connection structure are an integral member formed from a length of tubing as a single piece.

10. The connector defined in claim 1 wherein the first and second elongated members and the connection structure are an integral heat-set member formed from a length of nitinol tubing as a single piece.

11. The connector defined in claim 1 wherein the connection structure is bendable.

12. The connector defined in claim 1 wherein the connection structure bends sufficiently that the lateral spacing between the first and second elongated members may be reduced when the connector is placed inside a delivery tube.

13. The connector defined in claim 1 wherein the connection structure comprises a plurality of struts connected between the first and second elongated members that are bendable so that the lateral spacing between the first and second elongated members may be reduced when the connector is placed inside a delivery tube.

14. The connector defined in claim 1 wherein the connection structure is bendable so that the longitudinal shifting between the first and second elongated members may be reduced when the connector is placed inside a delivery tube.

15. A connector for forming an oblique-angle connection between a flexible tubular graft and an aperture in a portion of a patient's body organ tubing, comprising:

a first elongated member;

a second elongated member; and a connection structure connecting the first and second elongated members parallel to each other, the first and second elongated members being laterally spaced and longitudinally shifted with respect to each other so that the connector has at least one substantially oval open end for insertion in the aperture and supports connection of the flexible tubular graft to a portion of the body organ tubing of the patient at an oblique angle, wherein:
the connector has two ends; and
the connection structure comprises first and second pairs of struts, the first pair connecting said first and second elongated members at one end of the two ends of the connector and the second pair connecting said first and second elongated members at the other of the two ends of the connector.

16. A connector for forming an oblique-angle connection between a flexible tubular graft and an aperture in a portion of a patient's body organ tubing comprising:

a first elongated member having first and second edges;

a second elongated member having first and second edges, wherein the first and second edges of the first elongated member are substantially not in contact with the first and second edges of the second elongated member; and a connection structure connecting the first and second elongated members parallel to each other, the first and second members being laterally spaced and longitudinally shifted with respect to each other so that the connector has at least one substantially oval open end for insertion in the aperture and supports connection of the flexible tubular graft to a portion of the body organ tubing of the patient at an oblique angle, wherein:
at least one of the first and second elongated members has slots.

17. A connector for forming an oblique-angle connection between a flexible tubular graft and an aperture in a portion of a patient's body organ tubing, comprising:

a first elongated member;

a second elongated member; and a connection structure connecting the first and second elongated members parallel to each other, the first and second elongated members being laterally spaced and longitudinally shifted with respect to each other so that the connector has at least one substantially oval open end for insertion in the aperture and supports connection of the flexible tubular graft to a portion of the body organ tubing of the patient at an oblique angle, wherein:
at least one of the first and second elongated members has longitudinal slots.

18. A connector for forming an oblique-angle connection between a flexible tubular graft and an aperture in a portion of a patient's body organ tubing, comprising:

a first elongated member;

a second elongated member; and a connection structure connecting the first and second elongated members parallel to each other, the first and second elongated members being laterally spaced and longitudinally shifted with respect to each other so that the connector has at least one substantially oval open end for insertion in the aperture and supports connection of the flexible tubular graft to a portion of the body organ tubing of the patient at an oblique angle, wherein:
at least one of the first and second members has a continuous serpentine longitudinal slot.

* * * * *

UNITED STATES PATENT AND TRADEMARK OFFICE
CERTIFICATE OF CORRECTION

PATENT NO : 6,001,124

DATED : December 14, 1999

INVENTION(S) : OBLIQUE-ANGLE GRAFT CONNECTORS

It is certified that error appears in the above-identified patent and that said Letters Patent are hereby corrected as shown below:

Column 6, line 51, change "tublar" to --tubular--.

Signed and Sealed this

Twenty-second Day of May, 2001

Attest:

NICHOLAS P. GODICI

*Attesting Officer*   *Acting Director of the United States Patent and Trademark Office*